(12) United States Patent
Messner et al.

(10) Patent No.: US 6,482,344 B1
(45) Date of Patent: Nov. 19, 2002

(54) SUPERABSORBENT POLYMER FIBERS HAVING IMPROVED ABSORPTION CHARACTERISTICS

(75) Inventors: Bernfried A. Messner, Greensboro, NC (US); Whei-Neen Hsu, Greensboro, NC (US); Mark C. Joy, Greensboro, NC (US)

(73) Assignee: Stockhausen GmbH & Co. KG, Krefeld (DE)

( * ) Notice: Subject to any disclaimer, the term of this patent is extended or adjusted under 35 U.S.C. 154(b) by 77 days.

(21) Appl. No.: 09/644,385

(22) Filed: Aug. 23, 2000

(51) Int. Cl.$^7$ ............... D01D 5/24; D02G 3/00
(52) U.S. Cl. ............. 264/209.6; 264/182; 264/178 R; 264/211.12; 264/211.14; 264/211.17; 428/364; 428/397; 428/400
(58) Field of Search .................. 428/364, 397, 428/400, 394, 375, 359; 442/327, 335, 414; 264/182, 206, 205, 207, 211.11, 211.13, 211.17, 209.6, 211.14

(56) References Cited

U.S. PATENT DOCUMENTS

| | | |
|---|---|---|
| 3,939,123 A | 2/1976 | Matthews et al. |
| 3,940,542 A | 2/1976 | Knopf et al. |
| 4,128,692 A | 12/1978 | Reid |
| 4,187,342 A | 2/1980 | Holst et al. |
| 4,354,487 A | 10/1982 | Ocxzkowski et al. |
| 4,366,206 A | 12/1982 | Tanaka |
| 4,374,175 A | 2/1983 | Tanaka |
| 4,395,377 A | 7/1983 | Kondo et al. |
| 4,420,588 A | 12/1983 | Yoshioka et al. |
| 4,507,204 A | 3/1985 | Tanaka et al. |
| 4,552,905 A * | 11/1985 | Kell et al. .................. 521/149 |
| 4,587,308 A * | 5/1986 | Makita et al. ............... 525/373 |
| 4,600,407 A | 7/1986 | Huber |
| 4,616,063 A | 10/1986 | Le-Khac |
| 4,645,605 A | 2/1987 | Durham |
| 4,731,067 A | 3/1988 | Le-Khac |
| 4,743,244 A | 5/1988 | LeKhac |
| 4,801,647 A * | 1/1989 | Wolfe, Jr. .................... 525/74 |
| 4,813,945 A | 3/1989 | Le-Khac |
| 4,873,143 A | 10/1989 | Tanaka |
| 4,880,868 A | 11/1989 | Le-Khac |
| 4,892,533 A | 1/1990 | Le-Khac |
| 4,985,298 A * | 1/1991 | Buckley et al. ............. 428/288 |
| 5,026,784 A | 6/1991 | Le-Khac |
| 5,066,742 A | 11/1991 | Gupta |
| 5,079,306 A | 1/1992 | Le-Khac |
| 5,196,470 A | 3/1993 | Anderson et al. |
| 5,274,050 A | 12/1993 | Guo et al. |
| 5,409,771 A | 4/1995 | Dahmen et al. |
| 5,413,747 A | 5/1995 | Akers et al. |
| 5,447,788 A | 9/1995 | Rhim et al. |
| 5,466,731 A | 11/1995 | Akers et al. |
| 5,607,550 A * | 3/1997 | Akers ......................... 162/102 |
| 5,669,894 A * | 9/1997 | Goldman et al. ........... 604/368 |

FOREIGN PATENT DOCUMENTS

| | | | |
|---|---|---|---|
| GB | 2351742 | * | 1/2001 |
| WO | WO 00/56959 | * | 9/2000 |

OTHER PUBLICATIONS

"Health & Safety Information Sheet" (Jun. 1991); *Technical Absorbents Limited*.

"Material Safety Data Sheet" (Feb. 20, 1997); *Camelot*.

"OASIS Fibre Absorbent Product Data Sheet" (Jan. 6, 1999); *Technical Absorbents Limited*.

* cited by examiner

Primary Examiner—Cynthia H. Kelly
Assistant Examiner—J. M. Gray
(74) Attorney, Agent, or Firm—Smith Moore LLP

(57) ABSTRACT

A method for providing improved absorbency against pressure characteristics to non-surface crosslinked superabsorbent polymer fibers.

23 Claims, No Drawings

SUPERABSORBENT POLYMER FIBERS HAVING IMPROVED ABSORPTION CHARACTERISTICS

TECHNICAL FIELD

The present invention relates, in general, to polymers that absorb aqueous liquids (such as water, blood, and urine). More particularly, the present invention relates to superabsorbent polymers, namely polymers that absorb over 20 times their weight in water, and even more particularly, the superabsorbent polymers are in the form of fibers which have unique absorbency against pressure characteristics as compared to previously known superabsorbent polymer fibers.

Definitions of Abbreviations

| Abbreviation | Definition |
| --- | --- |
| AAP | absorbency against pressure |
| cm | centimeter |
| comp | comparison |
| X-linking | cross-linking |
| g | gram |
| hr | hour |
| μm | micrometer |
| mg | milligram |
| ml | milliliter |
| mm | millimeter |
| min | minute |
| DAP | 1,5-diaminopentane |
| BDE | 1,4-butanediol diolycidyl ether |
| DE | 1,3-butadiene diepoxide |
| ppm | parts per million |
| PEG | Polyethylene glycol |
| psi | Pounds per square inch |
| RH | relative humidity |
| sec | second (note, 1/60 of a minute) |
| NaOH | sodium hydroxide |
| SXL | Surface cross-linked |
| SAP | superabsorbent Polymer, a polymer that absorbs over 20 times its weight in water tea bag |
| TB | trifunctional polyethylene glycol |
| wt | weight |

BACKGROUND ART

SAPs, namely highly water-swellable polymers, typically are prepared from an aqueous mixture of monomers. Usually, one or more network X-linking agents are incorporated into the monomer mixture. For particulate SAP, after the polymerization and X-linking have ended, the viscous resultant is dried and subjected to mechanical grinding to create a desired particle size distribution. Alternatively for SAP fibers, the polymerized monomers are extruded into fibers, such as by forcing through an orifice (i.e., extruding through a spinneret) into a gaseous medium (i.e., a warm air current for drying) or by dry spinning (i.e., mono-component spinning or sheath-core composite spinning), and then the X-linking agent in the post-polymerized extrudate is activated, such as being heat-activated or photo-activated, to result in SAP fibers.

Particles of SAPs are made by two polymerization methods, namely the solvent or solution polymerization method and the inverse suspension or emulsion polymerization method. On the other hand, fibers of SAPs are made by the solvent or solution polymerization method.

As discussed in more detail below, SAPs are useful in various absorbent articles, due to the ability of the SAPs to absorb aqueous liquids in a ready manner. For instance, the journal article "Keeping Dry with Superabsorbent Polymers", *Chemtech*, (September, 1994) by Buchholz, contains an excellent discussion of various uses for SAPs, such as in sanitary articles (i.e., diapers, incontinence garments, etc.), in a sealing composite between concrete blocks that make up the wall of underwater tunnels, and in tapes for water blocking in fiber optic cables and power transmission cables. However, SAP fibers have found limited use due to poor absorbency against pressure and/or poor tensile strength, as opposed to SAP particulates which have good absorbency against pressure.

An excellent discussion of the manufacture of SAP fibers, for instance of polyacrylonitrile, can be seen in U.S. Pat. No. 4,873,143 (issued Oct. 10, 1989), U.S. Pat. No. 4,366,206 (issued Dec. 28, 1992), U.S. Pat. No. 4,374,175 (issued Feb. 15, 1983), and U.S. Pat. No. 4,507,204 (issued Mar. 26, 1985), all to Tanaka, assignor to Japan Exlan Company Limited.

Furthermore, an excellent discussion of the manufacture of SAP fibers, for instance of isobutylene/maleic anhydride copolymer, can be seen in U.S. Pat. No. 4,743,244 (issued May 10,1988), U.S. Pat. No. 4,813,945 (issued Mar. 21, 1989), U.S. Pat. No. 4,880,868 (issued Nov. 14,1989), U.S. Pat. No. 4,892,533 (issued Jan. 9, 1990), U.S. Pat. No. 4,731,067 (issued Mar. 15,1988), U.S. Pat. No. 5,026,784 (issued Jun. 25,1991), and U.S. Pat. No. 5,079,306 (issued Jan. 7, 1992), all to LeKhac, assignor to Arco Chemical Company.

Additionally, an excellent discussion of the manufacture of SAP fibers, for instance of acrylic acid/methyl acrylate copolymers, can be seen in U.S. Pat. No. 5,413,747 (issued May 9,1995), U.S. Pat. No. 5,466,731 (issued Nov. 14, 1995), and U.S. Pat. No. 5,607,550 (issued Mar. 4, 1997), all to Akers, assignor to Courtaulds Fibers (Holdings) Limited.

On the other hand, a good discussion of the methods for making SAP particles can be seen in U.S. Pat. No. 5,409,771 (issued Apr. 25, 1995) to Dahmen and Mertens, assignors to Chemische Fabrik Stockhausen GmbH. More specifically, this patent mentions that SAP particles are generally network X-linked polyacrylic acids or network X-linked starch-acrylic-acid-graft-polymers, the carboxyl groups of which are partially neutralized with sodium hydroxide or caustic potash, and that such SAP particles may be surface X-linked (which is discussed in detail below).

The disclosures of all patents and published patent applications that are mentioned are incorporated by reference.

SUMMARY OF THE INVENTION

A need still exists for SAP fibers with improved absorbency against pressure properties. A great advantage would be given to industry to provide such SAP fibers.

Therefore, the present invention provides a fiber comprising a surface cross-linked superabsorbent polymer fiber. Furthermore, the present invention provides an absorbent article comprising surface cross-linked superabsorbent polymer fibers. The resultant superabsorbent polymer fiber exhibits excellent absorbency against pressure characteristics, as measured by the AAP property test as defined below.

Also, the present invention provides a method for providing improved absorbency characteristics to superabsorbent polymer fibers. The method comprises providing superabsorbent polymer fibers that are free of a surface cross-linking treatment; mixing a surface cross-linking agent with the superabsorbent polymer fibers that are free of a surface cross-linking treatment; and heating the resultant mixture of the surface cross-linking agent and the superabsorbent polymer fibers that are free of a surface cross-linking treatment for a sufficient time at a sufficient temperature to achieve surface cross-linked superabsorbent polymer fibers having absorbency against pressure characteristics superior to the absorbency against pressure characteristics of the superabsorbent polymer fibers that are free of a surface X-linking treatment.

Additionally, the present invention affords a method for providing improved absorbency against pressure characteristics to superabsorbent polymer fibers in an absorbent article. The method comprises subjecting superabsorbent polymer fibers to a surface cross-linking treatment and forming an absorbent article from the resultant of the surface cross-linking treatment. The surface cross-linking treatment is accomplished by providing superabsorbent polymer fibers that are free of a surface cross-linking treatment; mixing a surface cross-linking agent with the superabsorbent polymer fibers that are free of a surface cross-linking treatment; and heating the surface cross-linking agent and the superabsorbent polymer fibers that are free of a surface cross-linking treatment for a sufficient time at a sufficient temperature to achieve surface cross-linked superabsorbent polymer fibers having absorbency against pressure characteristics superior to the absorbency against pressure characteristics of the superabsorbent polymer fibers that are free of a surface X-linking treatment.

Accordingly, it is an object of the present invention to provide a SAP fiber that obviates absorbency against pressure problems.

Moreover, it is an advantage of the present invention that an absorbent article employing the SAP fiber of the present invention exhibits little or no problems with SAP falling out from the edges of the absorbent article the way particulate SAP can.

Some of the objects of the invention having been stated, other objects and advantages will become evident as the description proceeds, when taken in connection with the Laboratory Examples described below.

DETAILED DESCRIPTION OF THE INVENTION

For the present invention, the inventive SAP fiber comprises non-surface X-linked SAP fiber, such as the olefin/alkyl carboxylate copolymer inorganic salts, i.e., isobutylene/maleic anhydride copolymer commercially available under the trade names CAMELOT 1241, CAMELOT 1231, CAMELOT 1038, CAMELOT 1031, and CAMELOT 1161 from Camelot Technologies Limited of Canada or such as the network X-linked acrylate based copolymers partially neutralized to the sodium salt, commercially available under the trade names OASIS 101, OASIS 111, and OASIS 121 from Technical Absorbents Limited of the United Kingdom, which non-surface X-linked SAP fiber is then surface X-linked.

After the surface X-linking treatment has been preformed in the present invention, the surface X-linked SAP fiber will typically have an AAP (performed at 0.6 psi, which is about 42 g/cm$^2$) above about 13 g/g, preferably above about 14 g/g, more preferably above about 15 g/g, even more preferably above about 16 g/g, and often as high as about 19 g/g to about 22 g/g, or even higher.

Thus, the inventive surface X-linked SAP fiber will exhibit a superior AAP property as compared to the same SAP fiber but not surface X-linked.

On the other hand, the TB retention capacity property of the surface X-linked SAP fiber typically is not as high as the TB retention capacity property of the same SAP fiber but not surface X-linked. The advantage afforded by a higher AAP of the surface X-linked SAP fiber more than offsets the small reduction in TB retention. The reason is that the fiber ends up in a web of fluff and fiber in an end use product, as described in detail below, and that end use product typically is subjected to pressure during use, such as a baby sitting on a disposable diaper. Thus, it is important that the AAP be high so that absorbed liquid does not come back out when pressure is applied.

The SAP fibers according to the present invention may be manufactured on a large scale by continuous or discontinuous processes. More specifically, the SAP fiber of use in the present invention may be manufactured by any of the prior art processes for making SAP fibers. For instance, techniques typically begin with an aqueous monomer solution, such as a solution of acrylic acid monomer, which is at least partially neutralized at some point. With solvent polymerization, the acid solution also contains a network X-linking agent. Next, polymerization is initiated with radical initiators, such as thermal, redox, or photo initiators. After completion of polymerization, fibers are usually formed by extruding an aqueous solution of the polymer in its non-X-linked state through a spinneret into a gaseous environment to remove the water to form a fiber or filament and subsequently X-linking the polymer, preferably by heating.

Thus, the SAP fiber may be obtained by polymerizing at least about 10%, more preferably about 25%, and even more preferably about 55 to about 99.9% by weight of monomers having olefinically-unsaturated groups, such as acrylonitrile groups, anhydride groups, carboxylic acid groups, or sulfonic acid groups. Such carboxylic acid groups include, but are not limited to, acrylic acids, methacrylic acids, and maleic acids. An example of a sulfonic acid group is 2-acrylamido-2-methylpropane sulfonic acid. The groups are present as salts, such as sodium, potassium, or ammonium salts, i.e., the acrylate salt of acrylic acid.

The acid groups are typically neutralized to at least about 25 mol %. Preferably, the extent of neutralization is to at least about 50 mol % up to about 80 mol %. More particularly, the preferred SAP fiber has been formed from X-linked acrylic acid or methacrylic acid, which has been partially neutralized. Suitable neutralizing agents are hydroxides and/or carbonates of alkaline earth metals and/or alkali metals, for instance, of Na, K, Li, Be, Mg, Fe, Co, Ni, and the like.

Additional useful monomers for making the SAPs include ethers, imides, amides (such as acrylamide, methacrylamide, and dimethyl aminopropyl acrylamide), maleic acid, maleic anhydride, vinyl chloride, vinyl alcohol, styrene, acryonitrile, isobutylene, isocyanate, esters (such as hydroxyethyl acrylate, hydroxypropyl acrylate, hydroxypropyl methacrylate, and dimethyl-aminoalkyl-methacrylate), and acrylamidopropyl trimethylammonium chloride.

Suitable network X-linking agents useful in making the SAP fibers include those which can be activated (such as heat activated or photo-activated) after post-polymerization extrusion of the fiber or filament, for instance, those which have one ethylenically unsaturated double bond and one functional group reactive toward acid groups, and those which are multi-functional, i.e., have several functional groups reactive toward acid groups. Suitable kinds of network X-linking agents include, but are not limited to, acrylate and methacrylate of polyols, such as hexapropylene glycol monomethacrylate. Suitable kinds of network X-linking agents that are multi-functional include, but are not limited to, alcohols, amines, and epoxides, such as tris(hydroxymethyl) aminomethane, ethylene diamine, and diisocyanate. These network X-linking agents are distinguished from and not to be confused with the surface X-linking agents discussed below.

Furthermore, depending on the desired end use, the SAP fiber may have a water-soluble polymeric component. The content may range from above 0 up to about 30% by weight of a component that includes, but is not limited to, partially or complete saponified polyvinyl alcohol, polyvinyl pyrrolidone, starch, starch derivatives, polyglycols, polyacrylic acids, and combinations thereof. The molecular weight of the component is not critical, provided that it is water-soluble. Preferred water-soluble polymeric components are starch, polyvinyl alcohol, and mixtures thereof. Preferably, the content of the water-soluble polymeric component in the SAP fiber ranges from about 1 to about 5% by weight, especially if starch and/or polyvinyl alcohol are present as the water-soluble polymeric component. Also, the water-soluble polymeric component may be present as a graft polymer having the acid-groups-containing polymer.

It is known from the above-discussed U.S. Pat. No. 5,409,771, to coat SAP particles with an alkylene carbonate followed by heating to effect surface X-linking.

More specifically, as described in U.S. Pat. No. 5,409,771, in order to coat the SAP particles with a surface X-linking agent (such as an alkylene carbonate, a polyol, a diamine, or a diepoxide), the SAP particles may be mixed with an aqueous-alcoholic solution of the surface X-linking agent. The amount of alcohol is determined by the solubility of the alkylene carbonate and is kept as low as possible for technical reasons, for instance, protection against explosions. Suitable alcohols are methanol, ethanol, butanol, or butyl glycol, as well as mixtures of these alcohols. The preferred solvent is water which typically is used in an amount of 0.3 to 5.0% by weight, relative to the particulate SAP. In some instances, the alkylene carbonate surface X-linking agent is dissolved in water, without any alcohol. It is also possible to apply the alkylene carbonate surface X-linking agent from a powder mixture, for example, with an inorganic carrier material, such as $SiO_2$, (see, lines 51–54 of column 4 of U.S. Pat. No. 5,409,771).

In the present invention, SAP fiber and surface X-linking agent may be mixed by the SAP fiber being coated with the surface X-linking agent, followed by heating to effect surface X-linking, as per the process of U.S. Pat. No. 5,409,771. Thus, the SAP fiber is surface X-linked. Additional to the disclosure of U.S. Pat. No. 5,409,771, it has been found with the present invention that (1) a ketone (such as acetone or methyl ethyl ketone) is another useful solvent besides water and/or various alcohols, (2) the surface X-linking agent may be mixed with the non-surface X-linked SAP fiber and heat supplied to effect surface X-linking absent the presence of any solvent and/or inorganic powder carrier, and (3) PEGs (such as PEG 200, PEG 300, PEG 600, or TPEG 990) are useful as a surface X-linking agent, in addition to usefulness of an alkylene carbonate, a diol, a diamine, or a diepoxide.

Compounds that have one or more groups capable of reacting with functional groups on the SAP may be employed as surface X-linking agents, which includes all surface X-linking agents specifically mentioned in U.S. Pat. No. 5,409,771. Multivalent ions and their salts are also suitable, as well as structures with multiple charges on their surface.

The following are suitable as surface X-linking agents. Alkylene carbonates are preferred and the following may be used as alkylene carbonates, e.g., 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxyethyl-1,3-dioxolan-2-one, 1,3-dioxan-2-one, 4-methyl-1,3-dioxan-2-one, 4,6-dimethyl-1,3-dioxan-2-one, 1,3-dioxepan-2-one, and combinations thereof. Preferred alkylene carbonates are 1,3,dioxolan-2-one and 4-methyl-1,3-dioxolan-2-one. A preferred diamine is 1,5-diaminopentane. Preferred diepoxides are 1,4-butanediol diglycidyl ether and 1,3-butadiene diepoxide. A preferred multivalent ion is trivalent aluminum.

To achieve the desired surface X-linking properties, the surface X-linking agent should be distributed evenly on the SAP fiber. For this purpose, mixing is effected in suitable mixers, such as fluidized bed mixers, paddle mixers, milling rolls, or twin-worm-mixers, or on a small scale, a standard household-type KITCHEN AID® mixer may be used.

According to U.S. Pat. No. 5,409,771, the thermal treatment which follows the coating treatment is carried out as follows. In general, the thermal treatment is at a temperature between 150 and 300° C. However, if the preferred alkylene carbonates are used, then the thermal treatment is at a temperature between 180 and 250° C. The treatment temperature depends on the dwell time and the kind of alkylene carbonate. At a temperature of 150° C., the thermal treatment typically is carried out for an hour or so. On the other hand, at a temperature of 250° C., a few minutes, e.g., 0.5 to 5 minutes, typically are sufficient to achieve the desired surface X-linking properties. With the present invention, a temperature as low as 90° C. may be employed. The thermal treatment may be carried out in conventional dryers or ovens. Examples of dryers and ovens include rotary kilns, fluidized bed dryers, disk dryers, or infrared dryers.

Sometimes, the inventive surface X-linked SAP fiber has a differential surface X-linking density. In other words, the fiber has a surface X-linking density toward the surface of the fiber which is greater than the surface X-linking density toward the interior of the fiber, i.e., toward the longitudinal axis of the fiber.

The inventive surface X-linked SAP fiber may be employed for any traditional use for which a SAP is employed. For instance, such uses include, but are not limited to, use in an absorbent article such as a sanitary article (i.e., diapers, incontinence garments, sanitary napkins, bandages, etc.), a sealing composite between concrete blocks that make up the wall of underwater tunnels (such as the Channel Tunnel connecting England and France, as mentioned in the above-noted Buchholz journal article), a tape or sheet for water blocking in fiber optic cables and power transmission cables (as also mentioned in the above-noted Buchholz journal article), a carrier (for insecticides, herbicides, and/or pesticides), an agricultural material (such as STOCKOSORB®, which is a SAP marketed by Stockhausen for use in agricultural fields to improve the capability of soils to keep water and nutrients near or with the roots of plants), a filtration sheet (such as for removal of water or moisture from gasoline, fuel, oil, organic solvent, and the like), and an absorbent liner in food packaging (and depending on the particular polymer in accordance with the regulations of the U.S. Food and Drug Administration, the liner may or may not be able to be in direct contact with the food).

As is well-known, absorbent articles are often made from a web, the web being made from SAP particles and fluff fibers by an air-laid process or a wet-laid process. Thus, the inventive web of surface X-linked SAP fiber together with fluff fibers may be made by an air-laid process or a wet-laid process.

Although the fluff fiber preferably is comminuted wood pulp (i.e., cellulosic fiber), for the fluff component of the web for the present invention, other wettable fibers such as cotton linters may be used. Furthermore, meltblown synthetic fibers such as polyethylene, polypropylene, polyesters, copolymers of polyesters and polyamides, and the like, may be employed. The fluff component may also be formed from a mixture of wood pulp fiber and one or more such meltblown synthetic fibers. For example, the fluff component may comprise at least about 5 weight %, preferably about 10 weight % meltblown synthetic fibers, and the remainder may comprise wood pulp fiber. The fibers of the web are generally hydrophilic or rendered hydrophilic through a surface treatment. Cellulosic fiber is preferred, and a preferred one is sold by Georgia Pacific under the trademark GOLDEN ISLES® 4800.

During the air-laid process or the wet-laid process, the weight ratio of the SAP fiber component to the fluff component typically is controlled to be in a range from about 90:10 to about 5:95. A very suitable SAP:fluff ratio is from about 30:70 to about 70:30.

More particularly, the inventive web of surface X-linked SAP fiber together with fluff (made by an air-laid process or a wet-laid process) exhibits an AAP property that is far superior to that of a web of non-surface X-linked SAP fiber together with fluff (made, respectively, by an air-laid process or a wet-laid process).

Test Methods

To characterize the SAP fibers as set out in the Laboratory Examples below (both those surface X-linked SAP fibers of the present invention, as well as those comparison commercially available non-surface X-linked SAP fibers), the tea bag retention capacity (TB), the absorbency against pressure (AAP), and the Multiple Rewet were measured in the following manner.

TB. The test was conducted at ambient conditions of temperature. The retention capacity of the fiber was determined according to the tea bag test method and reported as an average value of two measurements. Approximately 200 mg of SAP fiber were enclosed in a tea bag and immersed in 0.9% by weight NaCl solution for 30 minutes. Then, the tea bag was hung for 10 minutes, followed by being centrifuged at 1400 rpm for 5 minutes (centrifuge diameter was about 18 cm) and then weighed. Two tea bags without any SAP fiber were used as blanks.

Then, the TB was calculated according to the following equation:

$$TB=(W_3-W_2-W_1)/W_1$$

where,
  TB=Retention after an immersion time of 30 minutes (g of liquid absorbed/g of SAP fiber); the resultant TB value should be rounded to 2 significant figures
  $W_1$=Initial weight of SAP fiber (g)
  $W_2$=Weight of the average blank tea bags (without SAP fiber) after centrifugation (g)
  $W_3$=Weight of the tea bag with SAP fiber after centrifugation (g)

AAP. The test was conducted at ambient conditions of temperature. The purpose of the test is to determine the ability of each sample of SAP fiber to absorb fluid out of a reservoir while working under a pre-determined load or pressure. The fiber's absorbency of a 0.9% by weight NaCl solution (20±2° C.) under load was determined as follows.

The equipment used was a petri dish (diameter=150 mm; height=30 mm), fritted disc (catalogue No. 9520001223 from Kontes Glass), Whatman No. 3 round filter paper, a plastic spacer cup (weight=26.65±0.2 g, inner diameter=51±0.1 mm, outer diameter=60±0.1 mm), a stainless steel weight (weight=1166.5±0.05 g), an analytical balance (accuracy to 0.001 g), a stopwatch, a plexiglass cylinder with beveled edges (diameter=60 mm; height=50 mm), and a screen filter cloth (400 mesh=36 μm) on the bottom of the cylinder.

After allowing the fritted disc to soak in the NaCl solution for a minimum of 1 hour just prior to test use, the fritted disc was placed in the petri dish. Then, the NaCl solution was added to the petri dish so that the solution was slightly below the top of the fritted disc. Next, the Whatman filter paper was placed on top of the fritted disc, with thorough wetting of the filter paper with the NaCl solution, removing trapped air bubbles and avoiding any supernatant liquid.

The cylinder was tared on the analytical balance. An initial weight of 0.900±0.005 g of the SAP fiber sample was distributed onto the filter screen in cylinder bottom. The sample actual weight was recorded (E).

The plastic spacer and then the stainless steel weight were carefully placed into the cylinder. The weight of the completed AAP apparatus was recorded (A). The stainless steel weight exerted a pressure load of about 42 g/cm². (It is noted 42 g/cm²=0.6 psi.)

Then, the AAP apparatus was placed on the wet filter paper, allowing the SAP fiber sample to absorb the NaCl solution for 1 hour. During the entire test, the level of the NaCl solution was maintained to be slightly below the top surface of the fritted disc.

After the 1 hour, the apparatus with the swollen SAP fiber sample was re-weighed, and the weight recorded (B). The gram amount of the NaCl solution that had been retained per gram of fiber was calculated according to the following equation:

$$AAP=(B-A)/E$$

where,
  AAP is in g/g at 0.6 psi; the resultant AAP value should be rounded to 2 significant figures
  A is weight in g of AAP apparatus with SAP fiber prior to absorbing NaCl solution
  B is weight in g of AAP apparatus with SAP fiber after absorbing NaCl solution for 1 hour
  E is actual weight in g of SAP fiber MULTIPLE REWET. The purpose of this test was to determine the rate that a sample of a web of SAP and fluff (which represents a diaper) or a sample of an actual throwaway diaper acquires a quantity of liquid and the rewet behavior after this liquid addition. This procedure can be performed on any article (i.e., a real diaper or a sample of web material representing a diaper) that falls within the given size parameters. The results are useful in determining both how well the diaper article absorbs liquid and how well it retains the absorbed liquid.

The article is weighed, placed on the appropriate body-shaped test apparatus (colloquially known as a "kanga" boy version or a "kanga" girl version) as further described below, and subjected to a load.

A pre-determined quantity of test liquid is added to the article through the tube of the test apparatus onto the surface of the article. A stopwatch is used to determine the amount of time needed for all the liquid to completely empty the tube. Any leakage is recorded and re-introduced to the tube. After 20 minutes have passed, rewet measurements are carried out using a series of filter paper stacks under a constant load.

The article is then returned to the test apparatus for additional analysis where the liquid addition and rewet steps are repeated. Typically, there will be total of 3 liquid additions, 3 acquisition times, and 3 rewet measurements; however, additional repetitions are possible.

Definitions

Acquisition Time—The time between the addition of liquid and its complete infiltration into the article.

Rewet—The amount of liquid released onto the filter paper from the surface of the article.

Materials

Body-shaped test apparatus, "kanga" boy version or "kanga" girl version (a T-shaped holder onto the horizontal part of which is placed an oblong strip of web that is 20 cm across in order to place the strip into an arc shape with a 36 cm longitudinal diameter and a 21.5 cm transverse diameter, the difference being that the boy version has the tube, i.e., the vertical part of the T, displaced 5 cm off center toward the front of the strip).

Balance (accurate to 0.1 g).

3 weights for rewet measurement (1270-gram weights having a flat bottom surface with a diameter/width $\geq 9$ cm and $\leq 11$ cm).

Various weights (see paragraph 3 below under Procedure).

2 weigh boats, petri dishes, or similar containers.

Disposable pipettes for collecting leaked liquid.

Marker.

Ruler.

Tape.

Beaker (250 ml or 400 ml).

Graduated cylinder (100 ml or 250 ml).

Timer.

Filter paper, for quantitative analysis, fast; 9.0 cm diameter (e.g., Whatman 41).

Chemical for Test Liquid 0.9% NaCl solution (or other designated liquid).

Procedure

A minimum of duplicate determinations of the test are to be performed.

1. Weigh the dry diaper (WD) and mark the center of the article.
2. Place the diaper onto the kanga body-shaped test apparatus (boy or girl version) with the center of the diaper at the center of the kanga apparatus. In the case that the boy kanga is used, the tube must be pointing towards the front of the diaper (by 5 cm). Tape may be used to keep the diaper in place during the test.
3. Place the appropriate weight on each test apparatus being used. During the experiment, the total load for each diaper size is as follows (the weight of the test apparatus must be taken into account):

| Diaper Size (target child weight) | Total weight load |
|---|---|
| mini (<6 kg) | 4.5 kg |
| midi (4–9 kg) | 6.5 kg |
| maxi (8–18 kg) | 12.5 kg |
| maxi plus (10–20 kg) | 15.0 kg |
| junior (12–25 kg) | 18.0 kg |

4. Place weigh boats, petri dishes, or other similar containers directly under the edges of the "kanga" apparatus in order to capture any liquid that may escape during acquisition.

5. Fill one graduated cylinder for each test being performed with an appropriate quantity of test liquid. Record the amount of liquid used (liquid insult [ml]). The following chart lists typical liquid quantities:

| Diaper Size (target child weight) | Liquid Quantity |
|---|---|
| mini (<6 kg) | 40 ml |
| midi (4–9 kg) | 60 ml |
| maxi (8–18 kg) | 80 ml |
| maxi (8–18 kg) | 100 ml (if the retention is greater than 250 g) |
| maxi plus (10–20 kg) | 100 ml |
| maxi plus (10–20 kg) | 120 ml (if the retention is greater than 300 g) |
| junior (12–25 kg) | 120 ml |

6. Add the test liquid by pouring the contents of the graduated cylinder into the addition tube of the apparatus and record the amount of time needed for the tube to empty (acquisition time [seconds]). Start the timer for 20 minutes at the same time as the liquid is added to the diaper.
7. Immediately after acquisition is complete, the diaper should be checked for leakage. If liquid has escaped from the sides of the apparatus, it should be collected and the quantity of liquid is recorded (leakage [ml]). The liquid is poured back into the addition tube.
8. Weight out 3 filter paper stacks. The first and third stack should weigh approximately 30 grams each, while the second stack should weigh approximately 40 grams. The weight of each dry filter paper stack is recorded ($FD_{1,2,3}$)
9. After the 20 minutes time has expired, the diaper should be checked for any additional leakage or if any liquid has not been absorbed and remains in the tube. If either case, collect the liquid and record the amount (discard [ml]). Use a pipette to remove the liquid from the tube. This liquid is discarded.
10. Remove the diaper from the test apparatus and stretch it out on a table, and if it is an actual diaper, with the coverstock (topsheet) facing up. Use tape tabs to fasten the diaper onto the surface of the table.
11. Place the 3 pre-weighed filter paper stacks, as prepared in section 8 above, longitudinally in a row on the diaper. Stack #2 should be placed directly in the center of the diaper. Stacks #1 and #3 should be placed so that the distance between each stack is equal to the distance between the edge of the diaper and stacks #1 and #3. Stack #1 is placed closest to the tape tabs.
12. Place each of the 1270 g weights respectively onto each individual stack.
13. After 10 minutes, remove the weights and stacks of filter paper from the diaper, re-weigh the filter paper stacks, and record the wet weight of the filter paper as ($FW_{1,2,3}$).
14. Place the diaper back onto the test apparatus and reapply the appropriate load (according to the size of the diaper as described in the chart in section 3 above).
15. Repeat paragraphs 4–14 as many times as required. Typically, at least 3 repetitions are required.

Calculations $$R_{(1,2,3)} = FW_{(1,2,3)} - FD_{(1,2,3)} [g]$$

$$R_{total} = R_1 + R_2 + R_3 [g]$$

where $R_{(1,2,3)}$=Rewet of sections 1–3 [g]

$FW_{(1,2,3)}$=Wet filter paper, stacks 1–3 [g]
$FD_{(1,2,3)}$=Dry filter paper, stacks 1–3 [g]
$R_{total}$=Total Rewet [g]

$$AR\ [ml/min] = (LA-LL)/(AT/60)$$

where
  AR=Acquisition rate [ml/min]
  LA=Amount of liquid from section 5 above [ml]
  LL=Amount of liquid leaked during acquisition, as measured in section 7 above [ml]
  AT=Acquisition Time [sec]
Recording the Results
Size of the diaper (mini, midi, maxi, maxi plus or junior).
Weight of the dry diaper.
Amount of liquid used in each liquid addition [ml].
Load applied to diaper during acquisition [kg].
Acquisition time of each liquid addition [sec].
Acquisition Rate after adjusting for leakage [ml/min].
Total rewet after each liquid addition [g].
Leakage during each acquisition period [ml].
Discard after each acquisition period [ml].
Deviations from the method.
If testing is performed on a commercially available real diaper, also record the diaper brand name and diaper manufacturer.

LABORATORY EXAMPLES

The following concerns all examples.

Each percentage recited was a weight % unless specifically indicated otherwise as a mol %.

A commercially available non-surface X-linked SAP fiber, sold by Camelot Technologies Limited under the trade name CAMELOT or sold by Technical Absorbents Limited under the trade name OASIS, was employed as the starting material prior to treatment with various surface X-linking agents. 1,3-dioxolan-2-one was purchased from BASF, Hüls-AG, Texaco, or Creanova. Each of DAP, BDE, and DE was purchased from Aldrich Chemical Co., Milwaukee, Wis. The PEGs were purchased from Union Carbide. Acetone was purchased from Fisher Scientific.

Example 1

100 g of SAP fiber (CAMELOT 1241) was mixed in a KITCHEN AID® brand household mixer while a solution of 0.5 g of 1,3-dioxolan-2-one (as the surface X-linking agent), 4.0 g water, and 4.0 g acetone was sprayed onto the SAP fiber with an aerosol spray device (air brush kit from Paasche).

This resultant mixture was subsequently cured in a convection oven at a temperature between 90° C. to 200° C. for about 5 to 60 minutes. After cooling, the resulting surface X-linked SAP fibers were analyzed for retention (TB) and for absorption against pressure under a 0.6 psi weight (0.6 psi MP). The results are summarized in Table 1 below.

TABLE 1

| | 1,3-dioxolan-2-one (g) | $H_2O$ (g) | Acetone (g) | TB (g/g) | 0.6 psi AAP (g/g) |
|---|---|---|---|---|---|
| CAMELOT 1241 Fiber (comparison starting material) | — | — | — | 29.5 | 10.0 |
| Sample A | 0.5 | 4.0 | 4.0 | 23.5 | 22.0 |
| Sample B | 0.5 | 4.0 | 4.0 | 21.0 | 19.0 |
| Sample C | 0.5 | 4.0 | 4.0 | 22.0 | 18.0 |

| | Time (minutes) | Temperature (° C.) |
|---|---|---|
| Sample A | 20 | 160 |
| Sample B | 30 | 180 |
| Sample C | 20 | 180 |

Example 2

100 g of SAP fiber was surface X-linked with 0.7 g 1,3-dioxolan-2-one (as the surface X-linking agent), 4.0 g water, and 4.0 g of acetone using the procedure described above for Example 1. The results are summarized in Table 2 below.

TABLE 2

| | 1,3-dioxolan-2-one (g) | $H_2O$ (g) | Acetone (g) | TB (g/g) | 0.6 psi AAP (g/g) |
|---|---|---|---|---|---|
| CAMELOT 1241 Fiber (comparison starting material) | — | — | — | 29.5 | 10.0 |
| Sample D | 0.7 | 4.0 | 4.0 | 23.5 | 19.5 |
| Sample E | 0.7 | 4.0 | 4.0 | 20.0 | 20.0 |
| Sample F | 0.7 | 4.0 | 4.0 | 21.0 | 19.5 |
| Sample G | 0.7 | 4.0 | 4.0 | 18.0 | 19.0 |

| | Time (minutes) | Temperature (° C.) |
|---|---|---|
| CAMELOT 1241 Fiber (comparison starting material) | — | — |
| Sample D | 20 | 160 |
| Sample E | 20 | 170 |
| Sample F | 20 | 180 |
| Sample G | 20 | 190 |

Example 3

Either 1.0 g, 1.4 g, or 2.0 g of each of four different molecular weight PEG products (polyethylene glycol 200, polyethylene glycol 300, polyethylene glycol 600, and trifunctional polyethylene glycol 990) were each coated (as the surface X-linking agent) onto 100 g of SAP fiber using the procedure described above for Example 1. The results are summarized in Table 3 below.

TABLE 3

| | PEG 200 (g) | PEG 300 (g) | PEG 600 (g) | TPEG 990 (g) | $H_2O$ (g) | Acetone (g) | TB (g/g) | 0.6 psi AAP (g/g) | Time (minutes) | Temperature (° C.) |
|---|---|---|---|---|---|---|---|---|---|---|
| CAMELOT 1241 Fiber (comparison starting material) | — | — | — | — | — | — | 29.5 | 10.0 | — | — |
| Sample H | 1.4 | — | — | — | 4.0 | 3.3 | 23.5 | 17.0 | 20 | 170 |
| Sample I | 2.0 | — | — | — | 4.0 | 2.7 | 23.5 | 18.5 | 30 | 160 |
| Sample J | — | 1.0 | — | — | 4.0 | 3.5 | 24.0 | 19.5 | 20 | 170 |
| Sample K | — | 1.4 | — | — | 4.0 | 3.3 | 23.0 | 19.5 | 20 | 160 |
| Sample L | — | — | 1.4 | — | 4.0 | 3.3 | 23.5 | 16.5 | 30 | 160 |
| Sample M | — | — | 2.0 | — | 4.0 | 2.7 | 24.0 | 17.0 | 20 | 160 |
| Sample N | — | — | — | 1.4 | 4.0 | 3.3 | 25.0 | 16.0 | 20 | 170 |
| Sample O | — | — | — | 2.0 | 4.0 | 2.7 | 22.0 | 19.0 | 30 | 170 |

Example 4

Four other SAP fibers were each mixed with 1,3-dioxolan-2-one (as the surface X-linking agent) according to the procedure described above for Example 1 and heated in an oven from about 165° C. to 170° C. for approximately 25 to 40 minutes. Water and/or acetone were excluded (as solvents) in several coating mixtures in favor of a solution solely of heated 1,3-dioxolan-2-one. The results are summarized in Table 4 below.

TABLE 4

| | 1,3-dioxolan-2-one (g) | $H_2O$ (g) | Acetone (g) | TB (g/g) | 0.6 psi MP (g/g) |
|---|---|---|---|---|---|
| CAMELOT 1231 Fiber (comparison starting material) | — | — | — | 21.5 | 17.0 |
| Sample P | 0.5 | 4.0 | 4.0 | 20.0 | 18.0 |
| CAMELOT 1038 Fiber (comparison starting material) | — | — | — | 43.0 | 7.0 |
| Sample Q | 2.0 | — | 98.0 | 22.5 | 20.0 |
| CAMELOT 1031 Fiber (comparison starting material) | — | — | — | 22.5 | 18.0 |
| Sample R | 2.0 | — | — | 22.0 | 21.5 |
| CAMELOT 1161 Fiber (comparison starting material) | — | — | — | 38.0 | 7.5 |
| Sample S | 2.0 | — | 98.0 | 23.0 | 18.0 |

| | Time (minutes) | Temperature (° C.) |
|---|---|---|
| CAMELOT 1231 Fiber (comparison starting material) | — | — |
| Sample P | 20 | 165 |
| CAMELOT 1038 Fiber (comparison starting material) | — | — |
| Sample Q | 35 | 165 |
| CAMELOT 1031 Fiber (comparison starting material) | — | — |
| Sample R | 40 | 165 |
| CAMELOT 1161 Fiber (comparison starting material) | — | — |
| Sample S | 25 | 170 |

Example 5

100g of each of three other SAP fibers was coated with 1,3-dioxolan-2-one (as the X-linking agent) or PEG 200 (as the surface X-linking agent) using the procedure described above for Example 1. These materials were heated in an oven at about 165° C. for approximately 0.5 hour. Water and/or acetone were excluded (as solvents) in several coating mixtures in favor of a solution solely of heated 1,3-dioxolan-2-one. The results are summarized in Table 5 below.

TABLE 5

| | PEG 200 (g) | 1,3-dioxolan-2-one (g) | $H_2O$ (g) | Acetone (g) | TB (g/g) | 0.6 psi AAP (g/g) |
|---|---|---|---|---|---|---|
| OASIS 101 Fiber (comparison starting material) | — | — | — | — | 23.0 | 7.5 |
| Sample T | — | 2.0 | 4.0 | 4.0 | 21.0 | 15.0 |
| Sample U | 2.0 | — | 4.0 | 4.0 | 21.5 | 16.0 |
| OASIS 111 Fiber (comparison starting material) | — | — | — | — | 26.0 | 7.0 |
| Sample V | — | 2.0 | — | — | 24.0 | 18.0 |
| Sample W | 2.0 | — | — | — | 22.0 | 10.5 |
| OASIS 121 Fiber (comparison starting material) | — | — | — | — | 12.0 | 14.0 |
| Sample X | — | 2.0 | — | — | 12.0 | 16.0 |
| Sample Y | 2.0 | — | — | — | 12.0 | 15.5 |

| | Time (minutes) | Temperature (° C.) |
|---|---|---|
| OASIS 101 Fiber (comparison starting material) | — | — |
| Sample T | 30 | 165 |
| Sample U | 30 | 165 |
| OASIS 111 Fiber (comparison starting material) | — | — |
| Sample V | 30 | 165 |
| Sample W | 30 | 165 |
| OASES 121 Fiber (comparison starting material) | — | — |
| Sample X | 30 | 165 |
| Sample Y | 30 | 165 |

Example 6

100 g of each of two SAP fibers were coated with various mixtures of acetone and a surface X-linking agent (1,3-dioxolan-2-one; DAP; BDE; or DE), and then heated in an oven between about 90° C. to 200° C. between about 0.1 and 1.0 hour. The results are summarized in Table 6 below.

TABLE 6

| | 1,3-dioxolan-2-one (g) | Acetone (g) | TB (g/g) | 0.6 psi AAP (g/g) |
|---|---|---|---|---|
| CAMELOT 1241 Fiber (comparison starting material) | — | — | 29.5 | 10.0 |
| Sample Z | 4.0 | 96.0 | 22.0 | 20.0 |
| Sample AA | 8.0 | 92.0 | 26.5 | 14.5 |

| | DAP (g) | BDE (g) | DE (g) | Acetone (g) | TB (g/g) | 0.6 psi AAP (g/g) |
|---|---|---|---|---|---|---|
| CAMELOT 1241 Fiber (comparison starting material) | — | — | — | — | 29.5 | 10.0 |
| Sample BB | 8.0 | — | — | 92.0 | 23.8 | 15.9 |
| Sample CC | — | 2.0 | — | 98.0 | 20.3 | 15.5 |
| Sample DD | — | — | 2.0 | 98.0 | 20.3 | 14.3 |

| | 1,3-dioxolan-2-one (g) | Acetone (g) | TB (g/g) | 0.6 psi MP (g/g) |
|---|---|---|---|---|
| CAMELOT 1161 Fiber (comparison starting material) | — | — | 37.8 | 7.5 |
| Sample EE | 4.0 | 96.0 | 28.0 | 13.0 |
| Sample FF | 8.0 | 92.0 | 26.5 | 13.5 |

| | DAP (g) | BDE (g) | DE (g) | Acetone (g) | TB (g/g) | 0.6 psi AAP (g/g) |
|---|---|---|---|---|---|---|
| OASES 101 Fiber (comparison starting material) | — | — | — | — | 23.0 | 7.5 |
| Sample GG | 2.0 | — | — | 98.0 | 22.2 | 12.4 |
| Sample HH | — | 20 | — | 98.0 | 22.7 | 11.3 |
| Sample II | — | — | 2.0 | 98.0 | 19.0 | 9.6 |

| | Time (minutes) | Temperature (° C.) |
|---|---|---|
| CAMELOT 1241 Fiber (comparison starting material) | — | — |
| Sample Z | 15 | 190 |
| Sample AA | 45 | 150 |
| Sample BB | 10 | 175 |
| Sample CC | 30 | 100 |
| Sample DD | 30 | 100 |
| CAMELOT 1161 Fiber (comparison starling material) | — | — |
| Sample EE | 15 | 190 |
| Sample FF | 45 | 165 |
| OASIS 101 Fiber (comparison starting material) | | |
| Sample GG | 10 | 175 |
| Sample HH | 30 | 100 |
| Sample II | 30 | 100 |

As can be seen from the Tables, each sample of surface SAP X-linked fiber exhibited a superior AAP property as compared to the AAP property of the same SAP fiber prior to the surface X-linking treatment. Moreover, it was surprising that surface X-linking worked (1) with a PEG as the surface X-linking agent and (2) in the absence of a solvent, as neither of (1) or (2) is taught by the above-discussed U.S. Pat. No. 5,409,771.

Example 7

Webs of Surface X-linked SAP Fiber and Cellulosic Fluff Made by Air-Laid Process The inventive surface X-linked SAP fibers A and T made as described above in Examples 1 and 5, and their respective non-SXL SAP fiber precursors for comparison, were each respectively employed in a conventional air-laid process, using a laboratory scale Dan-Web machine, to make 4 webs with cellulosic fluff (for instance, fluff sold under the trademark GOLDEN ISLES® 4800 by Georgia Pacific). More specifically, the SAP was either CAMELOT 1241, CAMELOT 1241 that had been SXL with 1,3-dioxolan-2-one as per Sample A in Example 1, OASIS 101, or OASIS 101 that had been SXL with 1,3-dioxolan-2-one as per Sample T in Example 5. As is well known, such webs are useful in absorbent articles, such as sanitary napkins or disposable diapers.

The performance results were determined for the 4 air-laid webs that had been prepared using SAP and fluff in the Dan-Web machine. The multiple rewet parameters for these tests were as follows: 3×100 ml, 15 kg "kanga" girl version, center blot only. In addition to the total rewet and acquisition time results, the acquisition rate was calculated. The results are summarized in the Tables below.

TABLE 7A

Results for Multiple Rewet of Air-laid Cores Prepared with Superabsorbent Fiber Addition (grams).

| | (comp) CAMELOT 1241 | CAMELOT 1241 SXL with 1,3-dioxolan-2-one | (comp) OASIS 101 | OASIS 101 SXL with 1,3-dioxolan-2-one |
|---|---|---|---|---|
| Rewet 1 | 2.5 | 0.2 | 4.0 | 3.0 |
| Rewet 2 | 7.0 | 6.0 | 9.0 | 7.0 |
| Rewet 3 | 9.0 | 10.0 | 16.5 | 7.0 |
| Total Rewet | 18.5 | 16.2 | 29.5 | 17.0 |

TABLE 7B

Acquisition Time Results for Each Liquid Addition (sec).

| | (comp) CAMELOT 1241 | CAMELOT 1241 SXL with 1,3-dioxolan-2-one | (comp) OASIS 101 | OASIS 101 SXL with 1,3-dioxolan-2-one |
|---|---|---|---|---|
| Acquisition 1 | 310 | 235 | 361 | 253 |
| Acquisition 2 | 917 | 443 | 1179 | 503 |
| Acquisition 3 | 1807 | 730 | 1352 | 688 |

TABLE 7C

Acquisition Rate Results for Each Liquid Addition (ml/min).

| | (comp) CAMELOT 1241 | CAMELOT 1241 SXL with 1,3-dioxolan-2-one | (comp) OASIS 101 | OASIS 101 SXL with 1,3-dioxolan-2-one |
|---|---|---|---|---|
| Rate 1 | 19.0 | 39.0 | 10.0 | 30.0 |
| Rate 2 | 6.5 | 14.0 | 2.5 | 9.0 |
| Rate 3 | 3.0 | 4.0 | 1.5 | 5.0 |

As can be seen from the data, the instant invention reduced multiple rewet, decreased acquisition time, and increased acquisition rate, all desirable features.

Example 8

Webs of Surface X-linked SAP Fiber and Cellulosic Fluff Made by Wet-Laid Process The inventive surface X-linked SAP fibers A and T made as described above in Examples 1 and 5 are each respectively employed in a conventional wet-laid process, together with cellulosic fluff (for instance, fluff sold under the trademark GOLDEN ISLES® 4800 by Georgia Pacific) and tap water by mixing to form a slurry. The resultant slurry is poured into a web molder that is connected to a vacuum system in order to make webs. After the slurry is agitated, water is vacuum-drained from the slurry. As is well known, such webs are useful in absorbent articles, such as sanitary napkins, adult incontinence garments, or disposable diapers.

Each of the absorbent webs (as per the wet-laid process) incorporating SXL fibers should exhibit excellent multiple rewet performance, like the webs incorporating SXL fibers (as per the air-laid process) in Example 7.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for providing improved absorbency against pressure characteristics to non-surface cross-linked superabsorbent polymer fibers, said method comprising:
   (a) providing superabsorbent polymer fibers that are free of a surface cross-linking treatment;
   (b) mixing a surface cross-linking agent with the superabsorbent polymer fibers that are free of a surface cross-linking treatment; and
   (c) heating the resultant mixture of the surface cross-linking agent and the superabsorbent polymer fibers that are free of a surface cross-linking treatment for a sufficient time at a sufficient temperature to achieve surface cross-linked superabsorbent polymer fibers having absorbency against pressure characteristics superior to the absorbency against pressure characteristics of the superabsorbent polymer fibers that are free of a surface X-linking treatment
wherein said method is free of both a solvent and an inorganic powder carrier.

2. The method of claim 1, wherein the polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, acrylate polymers, isobutylene polymers, isocyanate polymers, maleic anhydride polymers, maleic acid polymers, network cross-linked products of any of the foregoing, and combinations thereof.

3. The method of claim 1, wherein the surface cross-linked superabsorbent polymer fibers exhibit absorbency against pressure characteristics superior to the absorbency against pressure characteristics of the superabsorbent polymer fibers free of a surface X-linking treatment.

4. The method of claim 3, wherein the surface cross-linked superabsorbent polymer fibers have a surface and a longitudinal axis, and wherein at least one of the fibers has a differential surface cross-linking density, wherein the surface cross-linking density toward the surface of the fiber is greater than the surface cross-linking density toward the longitudinal axis of the fiber.

5. The method of claim 1, wherein the surface cross-linking agent is selected from a compound that has at least one group capable of reacting with functional groups on the superabsorbent polymer.

6. The method of claim 5, wherein the surface cross-linking agent is selected from the group consisting of an alkylene carbonate, a polyol, a diamine, a diepoxide, a polyethylene glycol, a multivalent ion, and combinations thereof.

7. The method of claim 6, wherein the alkylene carbonate is selected from the group consisting of 1,3-dioxolan-2-one; 4-methyl-1,3-dioxolan-2-one; 4,5-dimethyl-1,3-dioxolan-2-one; 4,4-dimethyl-1,3-dioxolan-2-one; 4-ethyl-1,3-dioxolan-2-one; 4-hydroxyethyl-1,3-dioxolan-2-one; 1,3-dioxan-2-one; 4-methyl-1,3-dioxan-2-one; 4,6-dimethyl-1,3-dioxan-2-one; 1,3-dioxepan-2-one; and combinations thereof.

8. The method of claim 6, wherein the multivalent ion is trivalent aluminum.

9. The method of claim 6, wherein the diamine is 1,5-diaminopentane.

10. The method of claim 6, wherein the diepoxide is selected from the group consisting of 1,3-butadiene diepoxide, 1,4-butanediol diglycidyl ether, and combinations thereof.

11. The method of claim 6, wherein the polyethylene glycol is selected from the group consisting of polyethylene glycol 200, polyethylene glycol 300, polyethylene glycol 600, trifunctional polyethylene glycol 990, and combinations thereof.

12. A method for providing improved absorbency against pressure characteristics to superabsorbent polymer fibers in an absorbent article, said method comprising
   (i) subjecting superabsorbent polymer fibers to a surface cross-linking treatment by
      a. providing superabsorbent polymer fibers that are free of a surface cross-linking treatment;
      b. mixing a surface cross-linking agent with the superabsorbent polymer fibers that are free of a surface cross-linking treatment; and
      c. heating the resultant mixture of the surface cross-linking agent and the superabsorbent polymer fibers that are free of a surface cross-linking treatment for a sufficient time at a sufficient temperature to achieve surface cross-linked superabsorbent polymer fibers having absorbency against pressure characteristics superior to the absorbency against pressure characteristics of the superabsorbent polymer fibers that are free of a surface X-linking treatment;
   (ii) forming an absorbent article from the resultant step (i);
wherein said method is free of both a solvent and an inorganic powder carrier.

13. The method of claim 12, wherein the polymer is selected from the group consisting of hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, acrylamido-methylpropane-sulfonic acid terpolymers, acrylic acid polymers, methacrylic acid polymers, acrylate polymers, isobutylene polymers, isocyanate polymers, maleic anhydride polymers, maleic acid polymers, network cross-linked products of any of the foregoing, and combinations thereof.

14. The method of claim 12, wherein the surface cross-linked superabsorbent polymer fibers exhibit absorbency against pressure characteristics superior to the absorbency against pressure characteristics of the superabsorbent polymer fibers free of a surface X-linking treatment.

15. The method of claim 14, wherein the surface cross-linked superabsorbent polymer fibers have a surface and a longitudinal axis, and where at least one of the fibers has a differential surface cross-linking density, wherein the surface cross-linking density toward the surface of the fiber is greater than the surface cross-linking density toward the longitudinal axis of the fiber.

16. The method of claim 12, wherein step (ii) includes forming the absorbent article by mixing the surface cross-linked superabsorbent polymer fibers with a fluff component.

17. The method of claim 12, wherein the surface cross-linking agent is selected from a compound that has at least one group capable of reacting with functional groups on the superabsorbent polymer.

18. The method of claim 17, wherein the surface cross-linking agent is selected from the group consisting of an alkylene carbonate, a polyol, a diamine, a diepoxide, a polyethylene glycol, a multivalent ion, and combinations thereof.

19. The method of claim 18, wherein the multivalent ion is trivalent aluminum.

20. The method of claim 18, wherein the diamine is 1,5-diaminopentane.

21. The method of claim 18, wherein the diepoxide is selected from the group consisting of 1,3-butadiene diepoxide, 1,4-butanediol diglycidyl ether, and combinations thereof.

22. The method of claim 18, wherein the polyethylene glycol is selected from the group consisting of polyethylene glycol 200, polyethylene glycol 300, polyethylene glycol 600, trifunctional polyethylene glycol 990, and combinations thereof.

23. The method of claim 18, wherein the alkylene carbonate is selected from the group consisting of 1,3-dioxalan-2one; 4-methyl-1,3dioxolan-2-one; 4,5-dimethyl-1,3-dioxolan-2-one; 4,4-dimethyl-1,3-dioxolan-2-one; 4-ethyl-1,3-dioxolan-2-one; 4-hydroxyethyl-1,3-dioxolan-2-one; 1,3-dioxan-2one; 4-methyl-1,3-dioxan-2-one; 4,6dimethyl-1,3dioxan-2-one; 1,3dioxepan-2-one; and combinations thereof.

* * * * *